(12) United States Patent
Nollert

(10) Patent No.: US 9,161,808 B2
(45) Date of Patent: Oct. 20, 2015

(54) APPARATUS FOR ENDOBRONCHIAL ABLATION OF A TUMOR

(75) Inventor: Georg Nollert, Straβlach-Dingharting (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 872 days.

(21) Appl. No.: 13/418,383

(22) Filed: Mar. 13, 2012

(65) Prior Publication Data

US 2012/0239029 A1 Sep. 20, 2012

(30) Foreign Application Priority Data

Mar. 14, 2011 (DE) .......................... 10 2011 005 505

(51) Int. Cl.
| | |
|---|---|
| *A61B 18/12* | (2006.01) |
| *A61B 18/14* | (2006.01) |
| *A61M 25/10* | (2013.01) |
| *A61B 18/00* | (2006.01) |
| *A61M 25/06* | (2006.01) |

(52) U.S. Cl.
CPC ............ *A61B 18/1492* (2013.01); *A61M 25/10* (2013.01); *A61B 2018/00285* (2013.01); *A61B 2018/00541* (2013.01); *A61B 2018/00577* (2013.01); *A61B 2218/007* (2013.01); *A61M 25/0662* (2013.01); *A61M 2025/1047* (2013.01); *A61M 2025/1052* (2013.01)

(58) Field of Classification Search
CPC ............ A61B 2018/00577; A61B 2018/0022; A61B 2018/1861; A61B 17/00234; A61B 17/3468; A61B 2018/00285; A61B 2018/00541; A61B 2017/00809; A61B 2018/00291; A61B 2017/00238; A61B 2017/00336; A61B 2017/00743; A61B 17/00; A61B 2017/22051; A61B 2017/22067; A61B 5/6853; A61B 17/12022; A61B 18/00; A61B 1/00082; A61B 1/00094; A61B 2017/00544; A61B 2017/00597; A61B 5/0084; A61B 5/6852; A61M 25/00; A61M 2025/0681; A61M 25/10; A61M 25/0041; A61M 2025/1052; A61M 2025/1081; A61M 25/01; A61N 1/05; Y10T 29/49124; A61F 2/82; A61F 2/04
USPC ................................................ 606/32, 34, 41
See application file for complete search history.

(56) References Cited

U.S. PATENT DOCUMENTS 7,854,228 B2    12/2010  Wilson et al.
2009/0062788 A1*  3/2009  Long et al. ...................... 606/41

FOREIGN PATENT DOCUMENTS

| DE | 3542260 A1 | 6/1986 |
|---|---|---|
| DE | 4404253 A1 | 8/1995 |

(Continued)

OTHER PUBLICATIONS

Takanobu Suzuki et al. Percutaneous radiofrequency ablation for lung tumors beneath the rib under CT fluoroscopic guidance with gantry tilt Acta Radiologica, May 2010, vol. 51, No. 4: pp. 389-395; Magazine; 2010.

(Continued)

*Primary Examiner* — Deborah Malamud

(57) ABSTRACT

An apparatus for endobronchial ablation of a tumor is provided. The apparatus has an ablation catheter and a guide facility to be inserted into the bronchial system, a sheath defining a guide channel for the ablation catheter, a closing apparatus for a bronchial arm, and an aperture allowing airtight insertion of the ablation catheter into a bronchial arm blocked by the closing apparatus. The ablation catheter and/or the guide facility have a suction apparatus for sucking air out of a bronchial arm blocked off by the closing apparatus.

11 Claims, 1 Drawing Sheet

(56) References Cited

FOREIGN PATENT DOCUMENTS

| DE | 19932261 A1 | 1/2001 |
|---|---|---|
| DE | 60221139 T2 | 3/2008 |
| GB | 2168256 A | 6/1986 |

OTHER PUBLICATIONS

Complications after lung radiofrequency ablation: risk factors for lung inflammation M. Nomura et al. British Journal of Radiology, Mar. 81, 2008, pp. 244-249; Magazine; 2008.

M. Akeboshi et al., Percutaneous radiofrequency ablation of lung neoplasms: initial therapeutic response, J Vasc Interv Radiol. May 2004;15(5):463-70.; Others; 2004.

Terence C. Chua et al. Extending the survival of patients with melanoma lung metastases through radiofrequency ablation Acta Oncologica, 2010; 49: pp. 517-519; Magazine; 2010.

Michael D. Beland et al. Primary Non-Small Cell Lung Cancer: Review of Frequency, Location, and Time of Recurrence after Radiofrequency Ablation Radiology: vol. 254: No. 1-Jan. 2010 pp. 301-307; Magazine; 2010.

* cited by examiner

APPARATUS FOR ENDOBRONCHIAL ABLATION OF A TUMOR

CROSS REFERENCE TO RELATED APPLICATIONS

This application claims priority of German application No. 10 2011 005 505.3 filed Mar. 14, 2011, which is incorporated by reference herein in its entirety.

FIELD OF INVENTION

The invention relates to an apparatus for endobronchial ablation of a tumor.

BACKGROUND OF INVENTION

One standard procedure for removing lung tumors is surgical excision. Such operations require a thoracotomy and can require very major lung resections, depending on the position of the tumor in the lung and the size of the tumor. This puts a considerable strain on the patient.

As an alternative it has been proposed that tumors should be ablated, generally using high-frequency ablation. However this is currently only performed for tumors that have developed in the bronchi. Ablation is then palliative and only the bronchus is opened up by ablation so that a gas exchange can take place. Peripheral lung tumors can be punctured by means of a transcutaneous puncture and then ablated. However opening up the bronchi in this procedure can cause a pneumothorax, which causes the lung tissue to collapse.

Ablation, in particular high-frequency ablation, is only used palliatively in the prior art as an alternative to irradiation. This is because larger ablations, which could potentially be curative, produce large pulmonary fistulas, which cannot be controlled therapeutically. This is discussed for example in the articles by T. Suzuki et al., Percutaneous radiofrequency ablation for lung tumors beneath the rib under CT fluoroscopic guidance with gantry tilt, Acta Radiol. 2010 (4), 389-395 and M. Nomura et al., Complications after lung radiofrequency ablation: risk factors for lung inflammation, British Journal of Radiology, 81 (2008), 244-249. Also inadequate evaluation of the ablation result means that total ablation is only achieved in 39% of patients with a tumor larger than 3 cm (see also M. Akeboshi, Percutaneous Radiofrequency Ablation of Lung Neoplasms: Initial Therapeutic Response, J Vasc Intery Radiol, 2004 (15), pages 463-470). Only one solution for avoiding pulmonary fistulas during and after ablation is described in the cited article.

SUMMARY OF INVENTION

The object of the invention is therefore to specify an apparatus, which allows endobronchial ablation of a tumor with a greatly reduced risk of pulmonary fistulas and pneumothorax.

To achieve this object according to the invention an apparatus for endobronchial ablation of a tumor is provided, which comprises an ablation catheter and a guide facility to be inserted into the bronchial system, which has a sheath defining a guide channel for the catheter, a closing apparatus for a bronchial arm and an aperture allowing airtight insertion of the ablation catheter into a bronchial arm blocked by the closing apparatus, the ablation catheter and/or the guide facility comprising a suction apparatus to suck air out of a bronchial arm blocked off by the blocking apparatus.

According to the invention it is therefore proposed that a specially equipped ablation catheter should not simply be used but a guide facility should also be provided, so that the intervention site can be isolated as far as possible from respiration by the combined embodiment of the ablation catheter and the guide facility. Ablation of the lung tumor is therefore performed endobronchially by way of the special flexible ablation catheter. The ablation catheter is inserted through the guide channel in the sheath, to the distal end of which the closing apparatus is connected, which is able to block the bronchus, in the manner of the cuff of a breathing tube. In order not to cancel out such blocking by the closing apparatus by inserting the ablation catheter into the bronchus, an aperture is also provided, which allows essentially airtight insertion of the ablation catheter into the bronchus blocked by the closing apparatus. The ablation catheter can therefore be inserted into the bronchus at the treatment site, but the inflow of air through the guide channel is prevented. Since bronchial arms or bronchi also frequently have cross-connections, the invention also provides for the use of a suction apparatus to suck air out of the blocked off bronchus or bronchial arm, to prevent the pressure there becoming too high.

This apparatus described above also prevents air passing through the ablation catheter into the thoracic cavity when a bronchus is opened up and causing a pneumothorax, which would render a further therapeutic procedure impossible.

This allows transbronchial ablation of a lung tumor for the first time. The apparatus allows a completely novel, minimally invasive therapeutic procedure, which can potentially result in much lower morbidity for the patient than the procedure of the prior art.

The flexible sheath of the inventive apparatus can be made for example of plastic, as known in principle for an endotracheal tube.

In one advantageous embodiment of the present invention provision can be made for the closing apparatus to have a sleeve provided on the outside of the sheath with an inflatable balloon. The balloon can expediently be provided on the distal end of the sheath. Such sleeves with a balloon are known as cuffs in the case of endotracheal tubes. They allow particularly reliable closure of a bronchial arm, as a technology known in principle from another field of application is used. The balloon can expediently be made of silicon, as this has proved to be particularly well tolerated.

In one specific embodiment of the aperture, it can comprise at least one, in particular two non-return valves. It is preferable for two non-return valves to be used, to create a sort of "lock", through which the ablation catheter can be pushed out of the guide facility into the in particular already blocked bronchial aim. Non-return valves allow the catheter to enter, without allowing a flow of air to follow, which could have a negative influence on pressure conditions in the blocked bronchial arm.

To implement the at least one non-return valve in particular, the aperture can comprise at least one pierceable membrane made of an elastic material, in particular a rubber membrane. Such rubber membranes are known in principle and can also be used advantageously in the inventive apparatus. The rubber membrane is pierced by the ablation catheter and hugs the sides of the ablation catheter in such a manner that the most air-tight proximity possible results.

In one specific embodiment of the suction apparatus it can comprise a non-compressible lumen. This non-compressible lumen allows air sucked out of the blocked bronchial arm to be conducted outside. Provision should also be made for the suction apparatus to be operated during the entire intervention in order to maintain a lower pressure continuously.

The suction apparatus, which is integrated at least partially in the ablation catheter, can preferably comprise a lumen ending at at least one opening provided in the region of the catheter head and a proximally provided air suction facility, in particular a pump. This specific embodiment therefore disposes the point of action of the suction apparatus at the catheter head, therefore at the intervention site itself, so that the air is removed where this is actually necessary. To this end a non-compressible lumen can end for example at at least one opening provided in the region of the catheter head, with the actual suction process taking place by means of an air suction facility, for example a pump, provided proximally, in particular outside the body.

BRIEF DESCRIPTION OF THE DRAWINGS

Further advantages and details of the present invention will emerge from the exemplary embodiments described below and with reference to the drawing, in which.

DETAILED DESCRIPTION OF INVENTION

Figure 1:
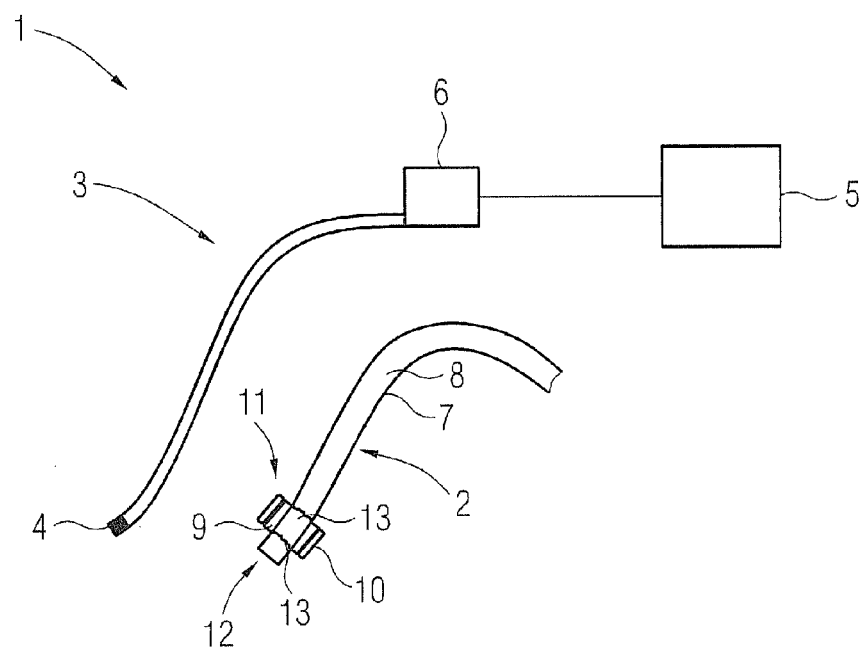
FIG. 1 shows an inventive apparatus.

FIG. 1 shows the basic components of an exemplary embodiment of an inventive apparatus 1. It comprises a guide facility 2 and an ablation catheter 3, which is to be passed through the guide facility 2 at a certain point in the bronchial system of a patient, where a lung tumor is to be ablated. The ablation catheter 3 therefore comprises ablation means 4 (only shown schematically here) at its distal end, for example for high-frequency ablation, which can be activated by a corresponding proximal catheter control device 5. As will be explained in more detail below, the ablation catheter 3 also comprises a pump 6 at its proximal end, said pump 6 being part of a suction apparatus for sucking air out of a blocked-off bronchial arm, as will be explained further with reference to FIG. 2.

The guide facility 2 first comprises a flexible sheath 7 made of plastic, which defines a guide channel 8 for the ablation catheter 3. Shown at the distal end of the guide facility 2 is a sleeve 9 around the sheath 7, which comprises an inflatable balloon 10 made of silicon. The sleeve 9 with the balloon 10 forms a blocking facility 11, by way of which a bronchus/bronchial arm can be isolated from the remainder of the bronchial system in respect of respiration.

Also located in the distal region of the sheath 7 is an aperture 12, which in the present instance comprises two rubber membranes 13 which form a lock and operate in the manner of a non-return valve and can be pierced by the ablation catheter 3.

Figure 2:
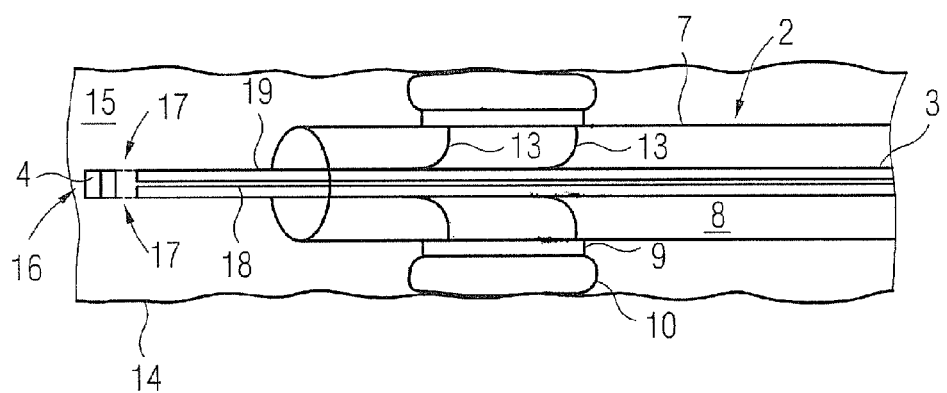
FIG. 2 shows an inventive apparatus in use.

FIG. 2 shows the inventive apparatus 1 in use in a bronchial arm 14. It shows the balloon 10 of the sleeve inflated and sealing off the region around the sheath 7. The ablation catheter 3 has been pushed through the guide channel 8, has pierced the rubber membranes 13 and now projects forwards out of the guide facility 2, so that it is possible to work in a region 15 blocked off by the blocking apparatus 11. It can be seen that a number of openings 17 are provided in the region of the tip 16 of the ablation catheter 3, said openings 17 being connected to a non-compressible lumen 18. Air is sucked from the region of the catheter tip 16 by the suction apparatus by means of the pump 6 through the non-compressible lumen 18 by means of the openings 17, so that a low pressure, which is independent of respiration, is maintained there even if there is a connection to other bronchi, thereby allowing a pneumothorax to be avoided during transbronchial ablation.

It should also be noted here that further lumens can also run in the catheter lumen 19, in addition to the lumen 18, for example to introduce washing fluids or the like, as well as control lines, in particular for the ablation means 4. These are not shown in detail here for the sake of clarity.

It should also be noted that it is in principle also possible to dispose the lumen 18 of the suction apparatus within the sheath 7, so that air is sucked away from the distal end of the sheath 7.

The invention claimed is:

1. An apparatus for endobronchial ablation of a tumor, comprising:
    an ablation catheter; and
    a guide device configured to be inserted into a bronchial system,
    wherein the guide device comprises:
        a sheath defining a guide channel for the ablation catheter,
        a closing device for blocking a bronchial arm, and
        an aperture for allowing airtight insertion of the ablation catheter into the bronchial arm blocked by the closing device,
    wherein the ablation catheter and/or the guide device comprises a suction apparatus for sucking air out of the bronchial arm blocked by the closing device,
    wherein the closing device comprises a sleeve and an inflatable balloon, and
    wherein the sleeve and the inflatable balloon are arranged around outside of the sheath of the guide device.

2. The apparatus as claimed in claim 1, wherein the balloon is made of silicon.

3. The apparatus as claimed in claim 1, wherein the aperture comprises at least one non-return valve.

4. The apparatus as claimed in claim 1, wherein the aperture comprises two non-return valves.

5. The apparatus as claimed in claim 1, wherein the aperture comprises at least one pierceable membrane made of an elastic material.

6. The apparatus as claimed in claim 5, wherein the pierceable membrane is a rubber membrane.

7. The apparatus as claimed in claim 1, wherein the suction apparatus comprises a non-compressible lumen.

8. The apparatus as claimed in claim 1, wherein the suction apparatus is at least partially integrated in the ablation catheter.

9. The apparatus as claimed in claim 1, wherein the suction apparatus comprises a lumen at an opening in a region of a head of the catheter.

10. The apparatus as claimed in claim 1, wherein the suction apparatus comprises an air suction device.

11. The apparatus as claimed in claim 10, wherein the air suction device is a pump.

* * * * *